United States Patent
Tsukamoto et al.

(10) Patent No.: US 6,619,107 B1
(45) Date of Patent: Sep. 16, 2003

(54) SIMPLE METHOD OF MEASURING NITROGEN OXIDE IN RUNNING VEHICLES

(75) Inventors: Tokihiro Tsukamoto, Kyoto (JP); Nobutaka Kihara, Kyoto (JP)

(73) Assignee: Horiba Ltd, Osaka (JP)

( * ) Notice: Subject to any disclaimer, the term of this patent is extended or adjusted under 35 U.S.C. 154(b) by 259 days.

(21) Appl. No.: 09/660,039

(22) Filed: Sep. 12, 2000

(30) Foreign Application Priority Data

Sep. 17, 1999 (JP) .......................................... 11-264470

(51) Int. Cl.⁷ ...................... G01M 19/00; G01N 33/497
(52) U.S. Cl. .................................... 73/118.1; 73/23.311
(58) Field of Search ................................ 73/116, 118.1, 73/23.31, 23.32; 60/286, 277, 301

(56) References Cited

U.S. PATENT DOCUMENTS 6,230,487 B1 * 5/2001 Blumenstock et al. ........ 60/286

FOREIGN PATENT DOCUMENTS

JP          11-023016   *  1/1999   .......... G01M/15/00

\* cited by examiner

*Primary Examiner*—Edward Lefkowitz
*Assistant Examiner*—Maurice Stevens
(74) *Attorney, Agent, or Firm*—Brian F. Swienton

(57) ABSTRACT

The present invention provides a simple method of measuring $NO_x$ in a running vehicle. While running on an actual road surface, the weight of $NO_x$ emitted from an engine of the running vehicle can be found more simply and accurately. The present invention comprises mounting a $NO_x$ analyzer, an air-fuel ratio sensor, and a data collection device on a vehicle, allowing the vehicle to run on the actual road surface, introducing the exhaust gas emitted while running on the actual road surface to a $NO_x$ analyzer to determine the concentration of $NO_x$ contained in the exhaust gas, determining a flow rate of the exhaust gas by using a fuel injection quantity based on a fuel injection pulse output from an electronic control unit mounted on the vehicle and an output from the air-fuel ratio sensor, and determining the weight of $NO_x$ emitted from the engine from the flow rate of the exhaust gas and the concentration of $NO_x$.

11 Claims, 2 Drawing Sheets

SIMPLE METHOD OF MEASURING NITROGEN OXIDE IN RUNNING VEHICLES

FIELD OF THE INVENTION

The present invention relates to a simple method of measuring the weight of nitrogen oxide emitted from an engine of a vehicle such as a motorcar running on an actual road surface.

DESCRIPTION OF THE PRIOR ART

As is well-known, nitrogen oxide (hereinafter referred, to as "$NO_x$") is one of the components determined as an air pollutant among gases (hereinafter referred to as "exhaust gas") emitted from an engine of a vehicle, e.g., motorcar. The concentration of $NO_x$ contained in the exhaust gas from the engine is greatest when operating in a city in terms of speed and load and is lower in other areas. It is therefore necessary to apply a moderate load to a motorcar when measuring the $NO_x$ emission.

In view of this, conventionally a motorcar is mounted on a chassis dynamometer, and allowed to run in accordance with a predetermined running pattern. The speed; torque and the like of the engine are regulated to apply a proper load to the motorcar, and a $NO_x$ analyzer, such as a chemiluminescent detector (CLD) is used to measure $NO_x$ contained in the exhaust gas.

However, in the aforementioned conventional technique, considerably large-scale equipment such as a chassis dynamometer is required in addition to a $NO_x$ analyzer. Facilities required for measurement increase measurement costs. The measurement of $NO_x$ using the chassis dynamometer unit is primarily conducted to measure $NO_x$ of motorcars, e.g., new cars, which have not yet been run. Motorcars which have been put to use, namely, the so-called used cars are usually not subjected to measurement using the chassis dynamometer unit. It is to be noted that the used car is measured in a fact-finding survey but its proportion is relatively low.

As aforementioned, to measure the concentration and weight of $NO_x$ emitted from a motorcar, the measurement is preferably made in such a condition that a proper running load is applied to the motorcar.

Meanwhile, applicant has applied a patent entitled "Simple Method Of Measuring Nitrogen Oxide In Running Vehicles" on Jan. 29, 1999 as a technique for simply measuring the weight of $NO_x$ emitted from an engine when a vehicle, e.g., motorcar, is allowed to run on an actual road surface (JP-A-11-23016). The method of measuring the weight of $NO_x$ according to this patent application has a system in which the flow rate of exhaust gas is determined using an intake air flow meter or an exhaust gas flow meter while measuring the concentration of $NO_x$ using a $NO_x$ analyzer to determine the weight of $NO_x$ emitted from an engine on the basis of the above $NO_x$ concentration and flow rate of exhaust gas in a simple manner.

However, since the flow rate of exhaust gas is determined using an intake air flow meter or an exhaust gas flow meter in the method of measuring the weight of $NO_x$ in the aforementioned patent application, the flow meter must be calibrated to determine the flow measurement. Also, pressure drop affords possibility for producing errors in the values measured of the exhaust gas flow rate and the point in question is open to further improvement.

The present invention has been conducted taking the above situation into consideration and one of the objects is to provide a simple method of measuring $NO_x$ in a running vehicle (hereinafter simply referred to as "$NO_x$ simple measurement method"). The method ensures that the weight of $NO_x$ emitted from the engine, while running the vehicle on an actual road surface, can be determined more simply and accurately.

SUMMARY OF THE INVENTION

The above object is attained by a $NO_x$ simple measurement method in accordance with the present invention. The method comprises mounting a $NO_x$ analyzer, an air-fuel ratio sensor, and a data collection device on a vehicle, allowing, the vehicle to run on an actual road surface, introducing the exhaust gas emitted from an engine to the $NO_x$ analyzer in order to determine the concentration of $NO_x$ contained in the exhaust gas, determining the flow rate of the exhaust gas by using the fuel injection quantity based on the fuel injection pulse output from an electronic control unit mounted on the vehicle and the output of the air-fuel ratio sensor, and determining the weight of $NO_x$ emitted from the engine from the flow rate of the exhaust gas and the concentration of $NO_x$.

In the $NO_x$ simple measurement method of the present invention, a vehicle is allowed to run on an actual road surface at varying speeds and gear ratios to thereby apply a proper load to the vehicle, and $NO_x$ is generated under the load. The concentration of $NO_x$ is then measured by a $NO_x$ analyzer mounted on the vehicle. On the other hand, the flow rate of the exhaust gas is found using the fuel injection quantity based on the fuel injection pulse output from an electronic control unit mounted on the vehicle and the output of the air-fuel ratio sensor. Accordingly, a given calculation is made using the flow rate of the exhaust gas and the concentration of $NO_x$ wherein the weight of $NO_x$ emitted from an engine can be found. Thus, the weight of $NO_x$ generated from an engine running on an actual road surface can be measured in real time.

When a direct insertion type $NO_x$ analyzer is used as the aforementioned $NO_x$ analyzer and is attached to an exhaust pipe connected to an engine, the structure of a measurement system is made simple.

DETAILED DESCRIPTION OF THE PREFERRED EMBODIMENTS

Figure 1:
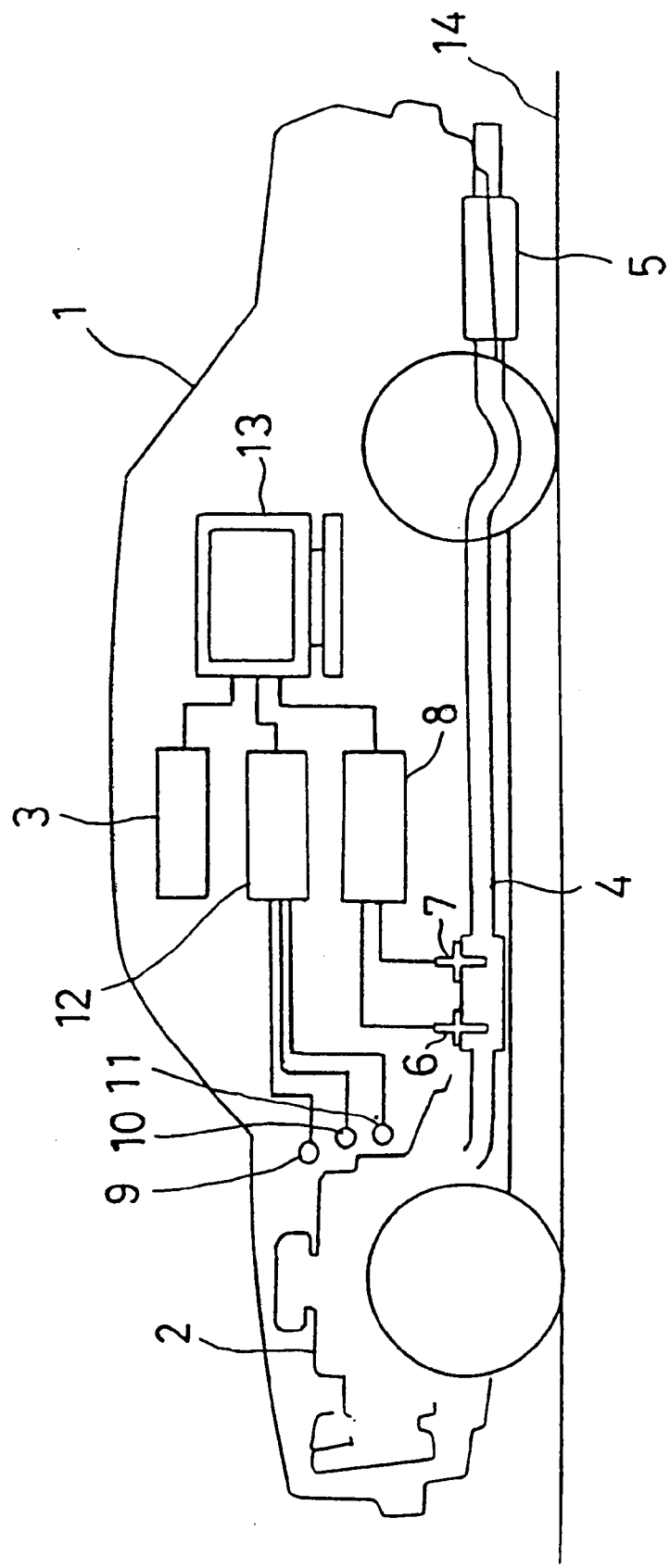
FIG. 1 is a schematic view illustrating an exemplary embodiment of a structure performing a $NO_x$ simple measurement method in accordance with the present invention.

FIG. 1 is a schematic view illustrating an exemplary $NO_x$ simple measurement method in accordance with the present invention. Reference numeral 1 represents a vehicle to be subjected to a test, for example, a used car, namely, a MT (Manual Transmission) car. Reference numeral 2 represents, for example, a gasoline engine (hereinafter referred to as "engine") of the used car 1. A fuel injection operation and the like are controlled by an electronic control unit (hereinafter referred to as "ECU") 3. The ECU 3 is structured so as to exchange data with a data collecting device. Reference numeral 4 represents an exhaust pipe connected to the engine 2 and reference numeral 5 represents a muffler disposed on the exhaust pipe 4. Reference numeral 6 represents a direct insertion type $NO_x$ sensor to measure the concentration of $NO_x$ disposed on an appropriate position of the exhaust pipe 4. An example of a direct insertion type $NO_x$ sensor 6 is a $NO_x$ sensor utilizing a zirconia solid electrolyte (e.g., a sensor manufactured by NGK Insulators, Ltd.). Reference numeral 7 represents an air-fuel ratio sensor which is disposed on the exhaust pipe 4 and placed at the side of the $NO_x$ sensor 6. Each output of these sensors 6 and 7 is input to a data collecting device (to be discussed below) through an interface 8.

Reference numerals 9, 10 and 11 respectively represent an engine speed sensor, a car speed sensor, and a temperature sensor for engine cooling water. Each output of the sensors 9 to 11 is input to the data collecting device (to be discussed below) through an interface 12.

Reference numeral 13 represents the data collecting device such as a microcomputer. The data collection device 13 is mounted on a suitable position of the used car process 1 and performs a timely calculation on the basis of signals from the ECU 3 and the sensors 9 to 11.

In addition, reference numeral 14 represents a road surface.

Referring back to FIG. 1, the $NO_x$ sensor 6 other than the engine speed sensor 9 and car speed sensor 10 is mounted for the measurement of $NO_x$ concentration. Therefore, by allowing the used car 1 to run on, for instance, the actual road surface 14, the concentration $C_{NOx}$ of $NO_x$ (wet condition), engine speed, and car speed can be measured in real time. Timely data processing of the measured data from the microcomputer 13 makes it possible to obtain in a simple manner the relationship between specific engine speed and the concentration of $NO_x$, the relationship between specific gear position/car speed and the concentration of $NO_x$, and the relationship between specific engine speed and the concentration of $NO_x$.

Meanwhile, the aforementioned concentration of $NO_x$ and flow rate (total flow rate: $Q_{EX}$) of exhaust gas are needed to calculate the concentration of $NO_x$ contained in the aforementioned exhaust gas. If the flow rate of exhaust gas is $Q_{EX}$, the amount of intake air is $Q_{Air}$, the weight of air is $G_{Air}$, the specific gravity of air is $\gamma_a$, the weight of fuel (gasoline) is $G_f$, and the air-fuel ratio is A/F, then the following relational formula is established between the parameters.

$$Q_{EX}=Q_{Air}+k\,G_f \quad (1)$$

$$Q_{Air}=Q_{GAir}/\gamma_a \quad (2)$$

$$Q_{Air}=Q_{Gf}\times A/F \quad (3)$$

where k is a known constant.

Using formulas (1) to (3), the following relational formula is obtained.

$$Q_{EX}=G_f\times[(A/F)\times(1/\gamma_a)+k] \quad (4)$$

A/F in formula (4) is detected by the air-fuel ratio sensor 7 disposed relatively close to the $NO_x$ sensor 6, and $\gamma_a$ and k are known constants. Therefore, if the fuel weight $G_f$ is detected, the flow rate $Q_{EX}$ of exhaust gas from the engine 2 can be determined using aforementioned formula (4).

Figure 2A:
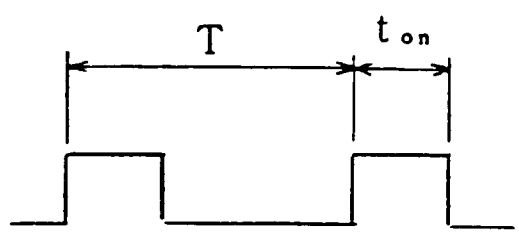
FIG. 2(A) is a graph showing an exemplary fuel injection pulse.
Figure 2B:
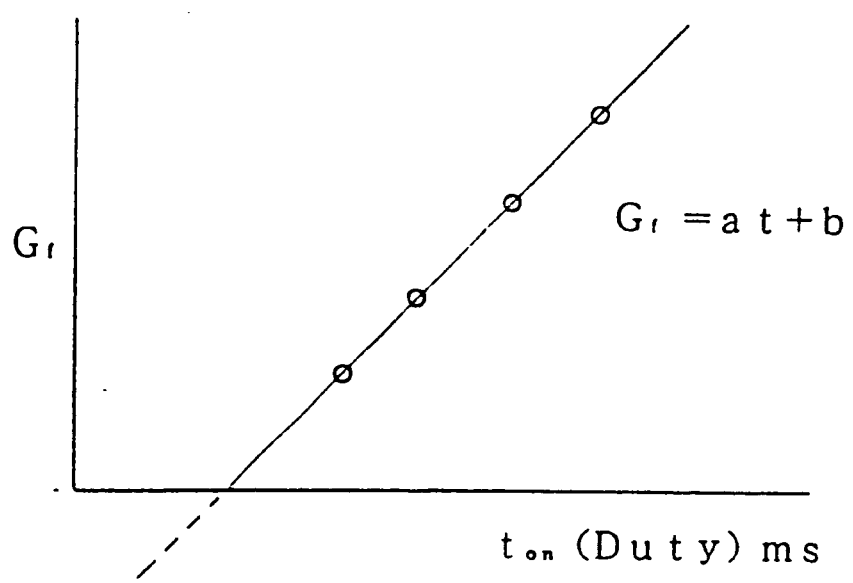
FIG. 2(B) is a graph showing the characteristic of an injector.

Meanwhile, the ECU 3 for controlling the engine 2 is mounted on the aforementioned used car 1, and a fuel injection pulse ($t_{on}$) as shown in FIG. 2(A) is output from a diagnostic terminal of the ECU 3. In FIG. 2(A), T is the cycle of the pulse which is ½ the rotational cycle of the engine 2.

By measuring the aforementioned fuel injection pulse ($t_{on}$), the fuel injection quantity (namely, the fuel weight $G_f$) can be accurately determined using a known calculation technique. Namely, the injector characteristic represented by the following formula and the fuel weight $G_f$ can be determined by measuring the fuel injection pulse.

$$G_f=at+b \quad (5)$$

where a and b are constants and t is time during which a valve is opened. From the known fuel weight $G_f$, the flow rate $Q_{EX}$ of exhaust gas is determined by using aforementioned formula (4). The flow rate $Q_{EX}$ of exhaust gas is revised in terms of humidity, temperature, and pressure to determined the flow rate $Q_{EX}$ of exhaust gas (wet condition).

In calculating the weight of $NO_x$ to be emitted, firstly $NO_x$ emission ratio $G_{NOx}$ must be found. The $NO_x$ emission ratio $G_{NOx}$ can be found by multiplying the above flow rate $Q_{EX}$ by the concentration $C_{NOx}$ of $NO_x$ and by the density (1.91 g/L) of $NO_x$. Specifically, the $NO_x$ emission ratio $G_{NOx}$ is shown by the following formula.

$$G_{NOx}=Q_{EX}\times C_{NOx}\times 10^{-6}\times 1.91\times 1000 \quad (6)$$

The amount of $NO_x$ to be omitted in the section where data is collected is determined by summing up a consumption every data sample. Specifically, when data is collected every second, it is $\Sigma G_{NOx}/60$. The value is divided by a running distance to thereby obtain the amount g/km of $NO_x$ to be emitted per unit running distance (e.g., 1 km).

In the aforementioned simple method of measuring $NO_x$, the concentration of $NO_x$ from the engine 2 when the used car 1 is allowed to run on the actual road surface 14 is measured by the $NO_x$ meter 6 attached to the exhaust pipe 4 connected to the engine 2. The air-fuel ratio is, measured by the air-fuel ratio sensor 7 attached to the exhaust pipe 4, and the fuel injection pulse output from the ECU 3, which controls the fuel injection quantity in the engine 2, is measured. Based on the pulse, the fuel injection quantity is calculated. The flow rate of exhaust gas emitted from the engine 2 is determined using the above air-fuel ratio and fuel injection quantity, and the weight of $NO_x$ emitted from the engine 2 is determined from the flow rate of exhaust gas and the above concentration of $NO_x$.

The concentration of $NO_x$ contained in exhaust gas emitted from the engine 2 can be therefore simply measured. Also, because the flow rate of exhaust gas is determined from the fuel injection quantity obtained based on the fuel injection pulse, no error caused by instruments is produced unlike the measurement method of the prior application entitled "Simple Method Of Measuring Nitrogen Oxide in Running Vehicles". Hence measuring results with high accuracy can be obtained despite its simplicity.

Particularly, because a direct insertion type $NO_x$ analyzer is used as the $NO_x$ analyzer and because the direct insertion type sensor 6 is attached to the exhaust pipe 4 connected to the engine 2 to measure the concentration of $NO_x$, the structure of the equipment for measuring $NO_x$ is made simpler than that of the conventional method using a chemiluminescent detector and the like.

Also, $NO_x$ can be continuously measured regardless of the amount of exhaust gas of the used car 1.

It is to be noted that the present invention is not limited to the used car 1 exemplified in the aforementioned embodiment, and that a so-called new car maybe used as the vehicle.

According to the present invention, as outlined above, the weight of $NO_x$, which is generated in and emitted from an engine running on an actual road surface and not in a simulated operation such as a chassis dynamometer, can be measured in real time. Thus, weight of $NO_x$ emitted from the used car 1, which is in a normal running condition, can be measured directly (in a live state). Also, the present invention ensures that the measurement of $NO_x$ can be made with high accuracy in spite of using simple equipment unlike the methods using a chassis dynamometer.

What is claimed is:

1. A simple method of measuring nitrogen oxide in a running vehicle comprising:

mounting a $NO_x$ analyzer, an air-fuel ratio sensor, and a data collection device on a vehicle;

running the vehicle on an actual road surface;

introducing the exhaust gas emitted during said running on the actual road surface to a $NO_x$ analyzer to determine the concentration of $NO_x$ contained in the exhaust gas;

determining a flow rate of the exhaust gas by using a fuel injection quantity based on a fuel injection pulse output from an electronic control unit mounted on the vehicle and an output from the air-fuel ratio sensor; and determining the weight of $NO_x$ emitted from the engine from the flow rate of the exhaust gas and the concentration of $NO_x$.

2. The method of claim 1, wherein said mounting a $NO_x$ analyzer further comprises providing a direct insertion type $NO_x$ sensor to measure the concentration of $NO_x$.

3. The method of claim 2, further comprising:

providing a data collecting device; and inputting each output of the direct insertion type $NO_x$ sensor and the air-fuel ratio sensor to the data collecting device.

4. The method of claim 3, further comprising:

providing an engine speed sensor, a car speed sensor, and a temperature sensor for engine cooling water; and inputting each output of the engine speed sensor, the car speed sensor, and the temperature sensor for engine cooling water to the data collecting device.

5. The method of claim 4, further comprising:

providing an electronic control unit to control a fuel injection operation;

wherein the data collecting device is a microcomputer.

6. The method of claim 5, wherein the concentration of $NO_x$, engine speed, and car speed are measured in real time;

wherein the microcomputer determines a relationship between the engine speed and concentration of $NO_x$; and wherein the microcomputer determines a relationship between specific gear position/car speed and the concentration of $NO_x$.

7. The method of claim 6, wherein an expression $Q_{EX}=G_f \times [(A/F) \times (1/\gamma_a)+k]$ is used for said determining of flow rate of the exhaust gas;

wherein $Q_{EX}$ is the flow rate of the exhaust gas;

wherein $G_f$ is the weight of fuel;

wherein A/F is the air-fuel ratio;

wherein $\gamma_a$ is the specific gravity of air; and wherein k is a known constant.

8. The method of claim 7, further comprising:

providing a fuel injection pulse ($t_{on}$);

outputting the fuel injection pulse ($t_{on}$) to a diagnostic terminal of the electronic control unit; and measuring the fuel injection pulse ($t_{on}$) to determine the weight of fuel ($G_f$) by using an expression $G_f=at+b$;

wherein a and b are constants; and wherein t is a time during which a valve is opened.

9. The method of claim 8, further comprising:

determining a $NO_x$ emission ratio using an expression $G_{NOx}=Q_{EX} \times C_{NOx} \times 10^{-6} \times 1.91 \times 1000$;

wherein $G_{NOx}$ is the $NO_x$ emission ratio; and wherein $C_{NOx}$ is the concentration of $NO_x$.

10. The method of claim 1, further comprising:

placing the air-fuel ratio sensor on an exhaust pipe of the engine.

11. A simple method of measuring nitrogen oxide in a running vehicle comprising:

mounting a $NO_x$ analyzer, an air-fuel ratio sensor and a data collection device on a vehicle;

running the vehicle on an actual road surface;

introducing exhaust gas emitted during said running on the actual road surface to a $NO_x$ analyzer to determine the concentration of $NO_x$ contained in the exhaust gas;

determining an injector characteristic (fuel injection time (t) to the fuel weight ($G_f$) characteristic) with respect to each vehicle by measuring in advance the fuel injection pulse outputted from the electronic control unit (ECU) or the like mounted to the vehicle, since the injector characteristic is usually different to each vehicle;

determining an actual measurement of the fuel weight ($G_f$) based on said injector characteristic while measuring said fuel injection time (t) during a running test;

calculating a flow rate of the exhaust gas ($Q_{EX}$) from the following equation using the determined fuel weight ($G_f$) and an output (A/F) of the air-fuel ration sensor:

$$Q_{EX}=G_f \times \{(A/f) \times (1/\gamma_a)+k\}$$

wherein, $\gamma_a$ denotes specific gravity of air (constant) and k is a known constant;

calculating a $NO_x$ mass emission using the following equation $$G_{NOx}=Q_{EX} \times C_{NOx} \times 10^{-6} \times 1.91 \times 1000$$

wherein, $G_{NOx}$ is the NOx mass emission, $Q_{EX}$ is the flow rate of the exhaust gas, and $C_{NOx}$ is the concentration on NOx; and calculating a NOx weight per kilometer using an expression NOx weight=$\Sigma\ G_{NOx}/L$, wherein, L is the running distance of the vehicle, and $\Sigma\ G_{NO}$ is the total mass of $No_x$.

* * * * *